(12) United States Patent
Lancon et al.

(10) Patent No.: US 7,097,351 B2
(45) Date of Patent: Aug. 29, 2006

(54) SYSTEM OF MONITORING OPERATING CONDITIONS OF ROTATING EQUIPMENT

(75) Inventors: Kevin C. Lancon, League City, TX (US); Keith D. Schindler, Newport News, VA (US)

(73) Assignee: Flowserve Management Company, Irving, TX (US)

( * ) Notice: Subject to any disclaimer, the term of this patent is extended or adjusted under 35 U.S.C. 154(b) by 0 days.

(21) Appl. No.: 10/675,207

(22) Filed: Sep. 30, 2003

(65) Prior Publication Data

US 2004/0213319 A1    Oct. 28, 2004

Related U.S. Application Data

(60) Provisional application No. 60/414,779, filed on Sep. 30, 2002.

(51) Int. Cl.
*G01K 17/06* (2006.01)
*G01K 1/12* (2006.01)
*G01N 11/14* (2006.01)

(52) U.S. Cl. .................... 374/4; 374/57; 374/141; 374/40

(58) Field of Classification Search ............. 374/153, 374/102, 57, 141, 120, 45, 4; 340/589, 682; 384/448, 624; 702/34, 130, 132, 134; 73/116, 73/168; 417/13, 32, 63; 277/317, 319
See application file for complete search history.

(56) References Cited

U.S. PATENT DOCUMENTS

| | | | |
|---|---|---|---|
| 3,921,435 A | 11/1975 | Howard | |
| 4,316,175 A * | 2/1982 | Korber et al. | 246/169 A |
| 4,691,276 A | 9/1987 | Miller et al. | |
| 4,773,766 A * | 9/1988 | Nagasaka et al. | 374/124 |
| 4,781,064 A | 11/1988 | Yates | |
| 4,796,142 A * | 1/1989 | Libert | 702/132 |
| 4,800,512 A * | 1/1989 | Busch | 702/182 |
| 4,814,870 A * | 3/1989 | Crall | 250/334 |
| 4,854,162 A | 8/1989 | Yerace et al. | |
| 4,885,707 A * | 12/1989 | Nichol et al. | 702/56 |
| 5,041,989 A | 8/1991 | Kataoka et al. | |
| 5,050,092 A | 9/1991 | Perry | |
| 5,076,589 A * | 12/1991 | Marsi | 277/394 |
| 5,115,406 A | 5/1992 | Zatezalo et al. | |
| 5,381,692 A | 1/1995 | Winslow et al. | |
| 5,386,117 A * | 1/1995 | Piety et al. | 250/358.1 |
| 5,533,413 A | 7/1996 | Kobayashi et al. | |

(Continued)

FOREIGN PATENT DOCUMENTS

EP    1124204 A2 *  8/2001

(Continued)

OTHER PUBLICATIONS

Rockwell International Corporation, ENTEK, "*The Ten Most Common Reasons Why Oil Analysis Programs Fail and the Strategies That Effectively Overcome Them*", Publication No. ENOAS-AT401A-EN-P, Mar. 2001, pp. 1-12.

(Continued)

*Primary Examiner*—Diego Gutierrez
*Assistant Examiner*—Oxana Maslova
(74) *Attorney, Agent, or Firm*—Flynn, Thiel, Boutell & Tanis, P.C.

(57) ABSTRACT

A monitoring system for rotating equipment includes detection of temperature conditions in various areas of the system including motor and pump bearings, mechanical seal environment including seal flush, seal cooler and seal reservoir and process fluid temperature. The monitoring system allows for the prediction of component failures and a proactive repair schedule which minimizes if not eliminates component damage.

15 Claims, 14 Drawing Sheets

U.S. PATENT DOCUMENTS

| | | | |
|---|---|---|---|
| 5,628,229 A | | 5/1997 | Krone et al. |
| 5,637,871 A | * | 6/1997 | Piety et al. ............... 250/358.1 |
| 5,691,707 A | | 11/1997 | Smith et al. |
| 5,762,342 A | | 6/1998 | Kakabaker et al. |
| 5,808,903 A | * | 9/1998 | Schiltz et al. ................... 702/56 |
| 5,907,491 A | * | 5/1999 | Canada et al. ............... 700/108 |
| 5,992,237 A | | 11/1999 | McCarty et al. |
| 6,006,164 A | | 12/1999 | McCarty et al. |
| 6,053,047 A | * | 4/2000 | Dister et al. ................... 73/593 |
| 6,065,345 A | | 5/2000 | Holenstein et al. |
| 6,078,874 A | * | 6/2000 | Piety et al. .................... 702/56 |
| 6,082,737 A | * | 7/2000 | Williamson et al. ......... 277/317 |
| 6,092,370 A | * | 7/2000 | Tremoulet et al. ............. 417/63 |
| 6,145,802 A | * | 11/2000 | Nakagaki et al. ....... 267/140.14 |
| 6,161,962 A | | 12/2000 | French et al. |
| 6,190,049 B1 | * | 2/2001 | Rose ........................... 384/121 |
| 6,199,018 B1 | * | 3/2001 | Quist et al. .................... 702/34 |
| 6,202,491 B1 | | 3/2001 | McCarty et al. |
| 6,208,953 B1 | | 3/2001 | Milek et al. |
| 6,236,328 B1 | | 5/2001 | Smith et al. |
| 6,241,383 B1 | | 6/2001 | Feller et al. |
| 6,260,004 B1 | | 7/2001 | Hays et al. |
| 6,271,761 B1 | | 8/2001 | Smith et al. |
| 6,289,735 B1 | | 9/2001 | Dister et al. |
| 6,297,742 B1 | | 10/2001 | Canada et al. |
| 6,312,226 B1 | * | 11/2001 | Senior et al. .................. 417/63 |
| 6,325,377 B1 | * | 12/2001 | Williamson et al. ......... 277/317 |
| 6,330,525 B1 | | 12/2001 | Hays et al. |
| 6,331,823 B1 | * | 12/2001 | El-Ibiary ............... 340/870.16 |
| 6,332,116 B1 | | 12/2001 | Qian et al. |
| 6,360,616 B1 | | 3/2002 | Halliday et al. |
| 6,425,293 B1 | | 7/2002 | Woodroffe et al. |
| 6,499,349 B1 | * | 12/2002 | Aronsson ...................... 702/56 |
| 6,505,143 B1 | * | 1/2003 | Lakshminarasimha et al. .......................... 702/183 |
| 6,584,434 B1 | * | 6/2003 | Schick et al. ............... 702/190 |
| 6,626,436 B1 | * | 9/2003 | Pecht et al. .................. 277/317 |
| 6,829,542 B1 | * | 12/2004 | Reynolds et al. .............. 702/34 |
| 2001/0001135 A1 | * | 5/2001 | Aronson ...................... 702/34 |
| 2001/0001136 A1 | * | 5/2001 | Aronsson ..................... 702/56 |

FOREIGN PATENT DOCUMENTS

| | | |
|---|---|---|
| EP | 909430 B1 * | 10/2001 |
| WO | WO 9801831 A1 * | 1/1998 |

OTHER PUBLICATIONS

ENTEK IRD and Flowserve Flow Solutions Division, Condition Data Point Monitoring™, "*Monthly Report—Complex 3/4 Machines*", Sep. 27, 2002, pp. 1-7.

ENTEK, Rockwell Automation, Integrated Condition Monitoring Solutions, "*Enwatch™ Online Surveillance System*" brochure, Publication No. ENOLS-TD302A-EN-P, Mar. 2002 (6 pages).

ENTEK, Rockwell Automation, Integrated Condition Monitoring Solutions, "*Enpac™ Family*" brochure, Publication No. ENPOR-TD101B-EN-P, Mar. 2002 (6 pages).

ENTEK, Rockwell Automation, "*ENTEK XM™—Machine Monitoring and Protection System*" brochure, Publication No. ENMON-PP105A-En-P, Sep. 2002 (4 pages).

* cited by examiner

SYSTEM OF MONITORING OPERATING CONDITIONS OF ROTATING EQUIPMENT

This application claims benefit of U.S. Provisional Application No. 60/414 779, filed Sep. 30, 2002.

FIELD OF THE INVENTION

The invention relates to a condition monitoring system for rotating equipment and, more particularly, to a system for detecting operating conditions of such rotating equipment in an effort to prevent equipment failures.

BACKGROUND OF THE INVENTION

Manufacturing and production facilities include rotating equipment therein such as motors and pumps. These motors and pumps include various components which may undergo wear or have equipment defects which cause failure of the components. Such components include bearings on the motor and pump, and mechanical seals which prevent leakage of the process fluid being pumped into the pump components along the shaft. Any failures of the components of the rotating equipment may cause significant expense both in the repair of the rotating equipment as well as down time during the manufacturing or processing of product.

In an effort to identify equipment damage prior to complete failure thereof, it is known to collect vibration data on the bearings of rotating equipment. Vibration data typically is collected on two locations on each of the motor and pump which locations correspond to the bearings therein. More particularly as to each bearing location, vibration data is collected for both the horizontal and vertical directions. It is important that the horizontal and vertical directions be at right angles and aligned with each other. In addition, to the horizontal and vertical data, axial data is collected for each of the motor and pump.

Vibration data can indicate equipment problems such as unbalance, bearing defects, gear defects, blade/impeller faults, structural resonance problems, rubbing, loss of lubrication, oil whirl, cavitation/recirculation problems, equipment distress and seal distress. As the equipment components begin to fail, vibration levels typically increase and if left undetected, catastrophic damage may occur to the equipment and result in extensive repair costs as well as lost production.

When increases in vibration levels lead to an indication of failure, repairs are required to the equipment although these repairs are less than when catastrophic failure is reached. Once the vibration levels increase, a window of time is provided between the start of excessive vibration and a catastrophic failure point such that it is critical to identify and correct and problems during this failure window. However, an undesirable feature associated with vibration analysis is that vibration is indicative of the presence of some damage such that this damage still must be repaired.

Furthermore, vibration analysis requires that the horizontal, vertical and axial vibration measurements be at precise orientations. This may be difficult, however, for measurements taken with handheld vibration detectors, particularly where the equipment material is non-metallic. For example, if a horizontal measurement is not taken perpendicular to the vertical measurement, results would be affected. Accordingly, use of manual vibration detectors is more likely to introduce human error into the process, although the use of handheld measurement devices remains desirable since this is more cost effective than using a fully automated sensing system comprising permanent sensors and monitoring equipment.

It is an object of the invention to provide a system of monitoring rotating equipment which proactively or predictively identifies component problems prior to the occurrence of damage in the rotating equipment.

The invention relates to a monitoring system which collects temperature data of critical areas on the rotating equipment. This temperature monitoring system is capable of detecting problems before damage occurs and may be used in combination with vibration analysis and other sampling techniques to provide a comprehensive monitoring system for the rotating equipment.

Generally, the temperature monitoring system of the invention monitors bearing temperatures in the motor and pump, the process fluid temperature and various areas of the mechanical seal environment including seal flush, seal cooler and seal reservoir. Typically, unusual fluid flow in the equipment components generates undesirable and out of the ordinary heat which causes temperature increases that may be detected before actual failure and damage of the components. This may significantly reduce repair costs and down time of the rotating equipment.

The condition monitoring system furthermore provides more reliable results with bearings since only a single temperature reading is made on each bearing wherein the temperature reading does not require that the temperature detector be oriented at a precise angle. Still further, the temperature monitoring system allows other equipment environments to be monitored, particularly, the seal environment wherein conditions leading to failure cause little if any vibration.

Other objects and purposes of the invention, and variations thereof, will be apparent upon reading the following specification and inspecting the accompanying drawings.

Figure 1:
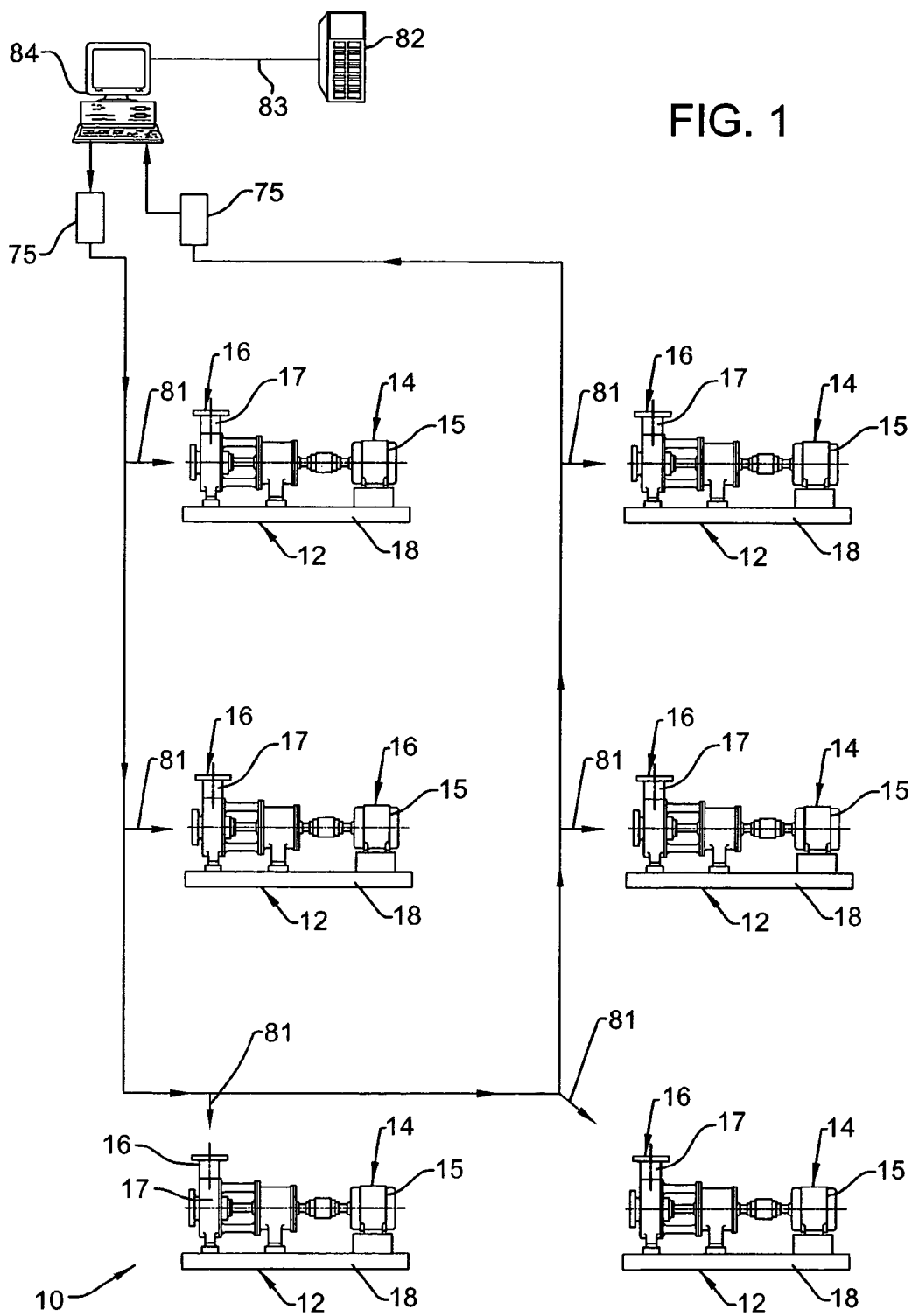
FIG. 1 is a diagrammatic plan view of a processing facility having a plurality of machines and an on-site computer terminal for analyzing data.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. Said terminology will include the words specifically mentioned, derivatives thereof, and words of similar import.

DETAILED DESCRIPTION

Referring to FIG. 1, the invention relates to a condition monitoring system for rotating equipment, wherein temperature data is periodically collected for the equipment and analyzed to identify abnormal operating conditions. Such abnormal operating conditions, if left uncorrected, would eventually lead to failure of the rotating equipment. However, the monitoring system of the invention is capable of providing early warning of abnormal conditions before significant damage occurs to the rotating equipment. This temperature monitoring may be conducted by itself but preferably is conducted in combination with vibration monitoring.

Generally, a manufacturing or processing facility or plant 10 includes multiple machines 12 therein. FIG. 1 diagrammatically illustrates a layout of rotating equipment type machines 12 although the physical location and construction of the machines 12 varies widely from facility to facility. It will be understood that the layout of FIG. 1 is for illustrative purposes and that the system of the invention as described herein may be readily adapted to any facility.

Each machine 12 typically includes a drive component 14, such as a motor 15, and a driven component 16, such as a pump 17. The drive and driven components 14 and 16 are mounted on a base frame 18. It will be understood that the driven component 16 may also be a compressor, fan, gearbox or the like and the term "fluid" herein may refer to a liquid or a gas.

Figure 2:
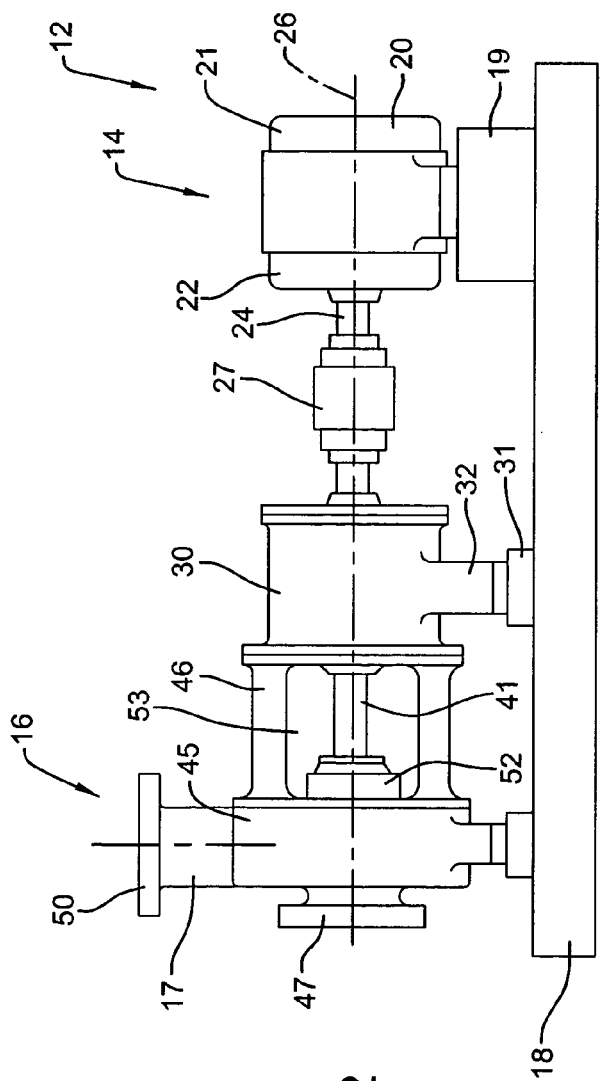
FIG. 2 is an enlarged side elevational view of one machine comprising rotating equipment which includes a pump and motor therefor.

Referring to FIG. 2, the electric motor 15 is mounted on a pedestal 19 and has a housing 20 which includes an outboard end 21 and an inboard end 22. A pair of motor bearings are enclosed within the motor housing 20 proximate the opposite ends 21 and 22 respectively. These bearings support a rotatable drive shaft 24 which extends axially from the inboard end 22 and rotates about axis 26. The terminal end of the drive shaft 24 includes a shaft coupling 27.

Figure 4:
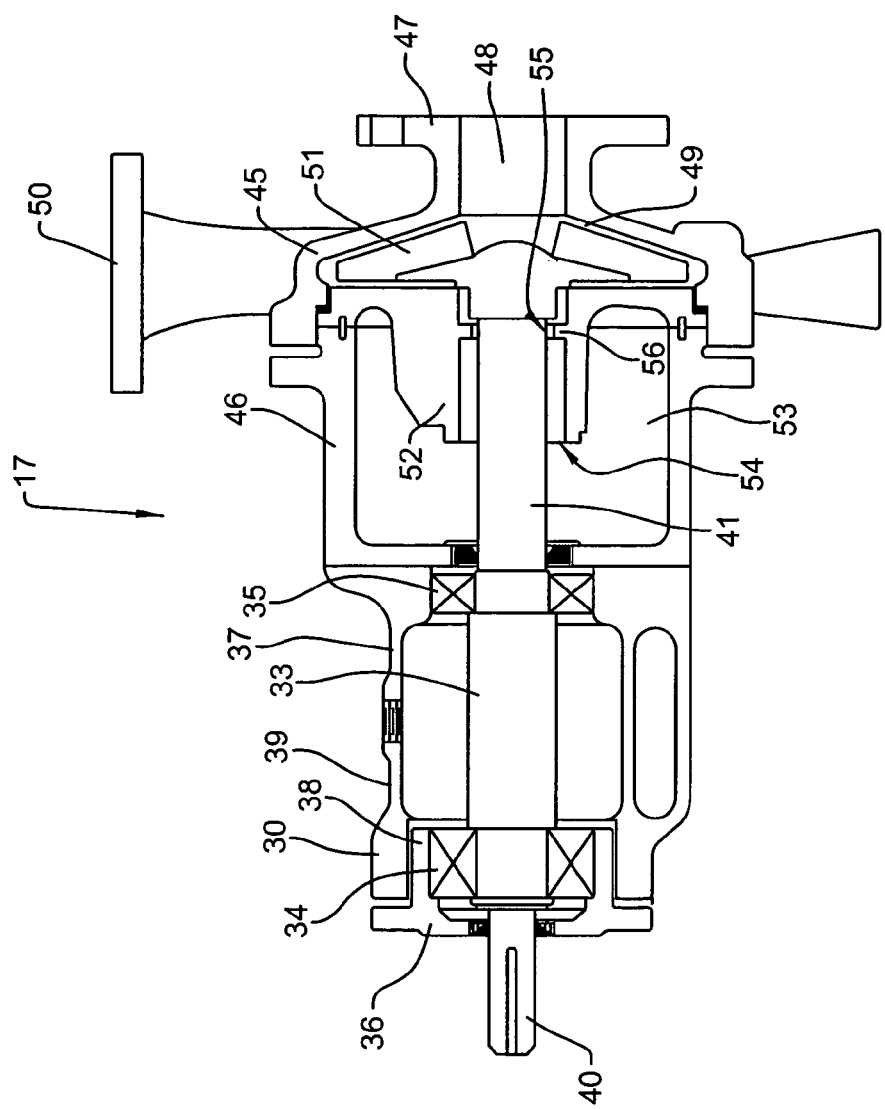
FIG. 4 is a side cross sectional view of the pump.

The pump 17 includes a bearing housing 30 which is supported vertically on a pedestal 31 by a housing mount 32. Referring to FIGS. 2 and 4, the bearing housing 30 is generally cylindrical and includes a pump shaft 33 extending axially therethrough. The pump shaft 33 is rotatably supported by an outboard thrust bearing 34 and an inboard radial bearing 35. The thrust bearing 34 is supported within the housing 30 within an annular flange 38 of an end cap 36.

The bearing 35 directly contacts a housing wall 37 while the bearing 34 is supported on the wall 37 by the annular flange 38 on the end cap 36. The annular flange 38 mutually contacts the bearing 34 and the housing wall 37. In view of the foregoing, heat generated in the bearings 34 and 35 is conducted radially to the exterior housing surface 39.

The outboard end 40 of the pump shaft 33 projects axially from the bearing housing 30 and is connected to the coupling 27 in coaxial alignment with the motor shaft 24 so as to rotate in unison therewith. The inboard end 41 of the pump shaft 33 projects from the bearing housing 30.

Referring to FIG. 4, the pump 17 further includes a pump casing 45 and a seal housing 46 disposed intermediate the pump casing 45 and bearing housing 30. The pump casing 45 includes an inlet 47 that defines the suction eye 48 thereof which opens axially into an impeller chamber 49. The impeller chamber 49 opens radially into an outlet or discharge port 50 and includes a rotary impeller 51 therein. The pump shaft 33 projects axially into the impeller chamber 49 and is affixed to the impeller 51 so as to effect rotation thereof.

The pump 17 further includes a stuffing box 52 which opens axially into a seal chamber 53. The stuffing box 52 has an inboard end 54 which is spaced radially outwardly of the shaft 30 and an outboard end 55 which is constricted radially to define a throat 56 that communicates with the impeller chamber 49.

When the pump shaft 33 is driven by the motor 15, the impeller 51 rotates within the impeller chamber 49 in a conventional manner. The inlet 47 allows a process fluid 58 to flow into the impeller chamber 49 as seen in FIG. 10 whereby the impeller 51 discharges the process fluid 58 through the outlet 50 under pressure.

Figure 10:
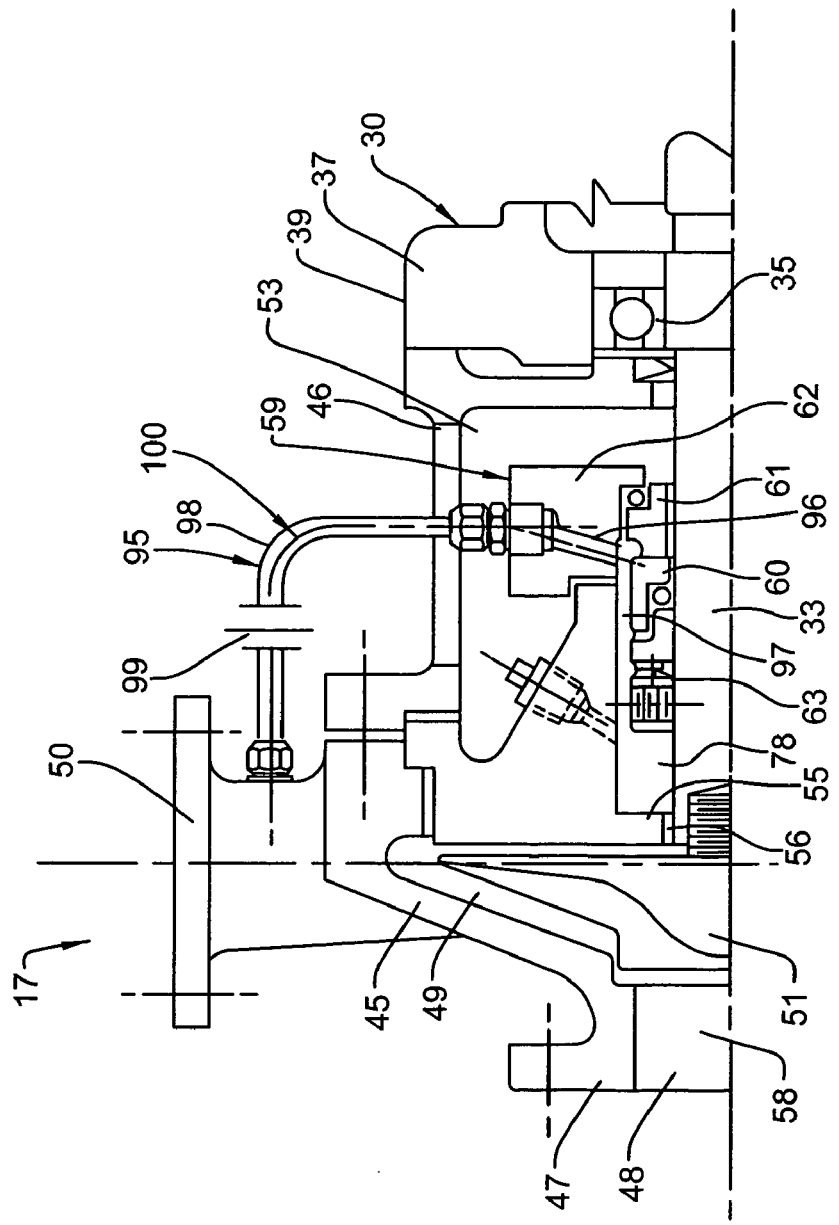
FIG. 10 is a more detailed partial cross sectional side view of the pump and seal.

To prevent leakage of the process fluid 58 axially along the shaft 33 through the stuffing box 52, a mechanical seal is mounted to the stuffing box 52 such as the single mechanical seal 59 illustrated in FIG. 10. The mechanical seal 59 includes a pair of relatively rotatable annular seal rings 60 and 61. A seal gland 62 is fastened to the stuffing box 52 and supports the seal ring 61 non-rotatably thereon. The other seal ring 60 is rotatably supported on the shaft 33 by a shaft sleeve 63. A more detailed discussion of the mechanical seal environment will be provided herein.

During operation of the machine 12, the various bearings in the motor 14 and the pump 17 may begin to wear, which could cause vibrations, or may be subject to vibrations due to abnormal conditions associated with the rotatable components of the machine 12 such as in the impeller 51 or due to cavitation or recirculation problems in the process fluid 58.

To identify such vibrations, it is known to collect vibration data on the machine 12. In particular, it is known to measure vibration levels occurring in the motor 15 and pump 17 in an effort to identify abnormal operating conditions. Such vibration measurements are taken adjacent the bearings of the pump 17 and motor 15.

Figure 3:
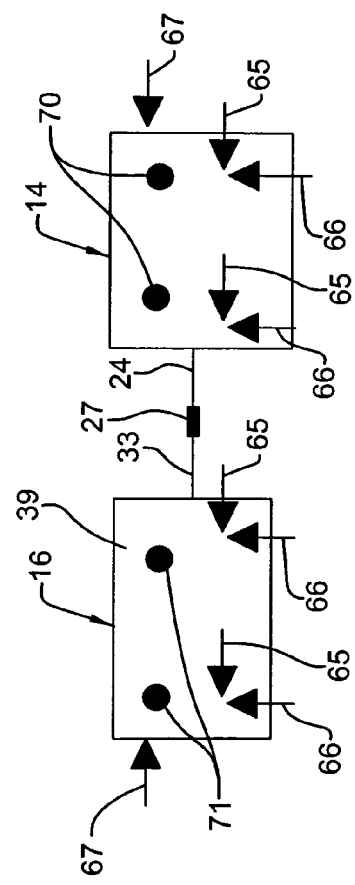
FIG. 3 is a diagrammatic view of vibration detection locations and temperature collection locations on the rotating equipment.

FIG. 3 diagrammatically illustrates a drive component 14, such as a motor, and a driven component 16, wherein the components 14 and 16 have respective shafts 24 and 33 that are interconnected by a coupling 27. To monitor vibrations, handheld data collection units have been used to collect vibration data through a magnetic vibration sensor 64 which attaches to the metal housings of the drive component 14 and the driven component 16 as diagrammatically illustrated in FIG. 6.

Figure 6:
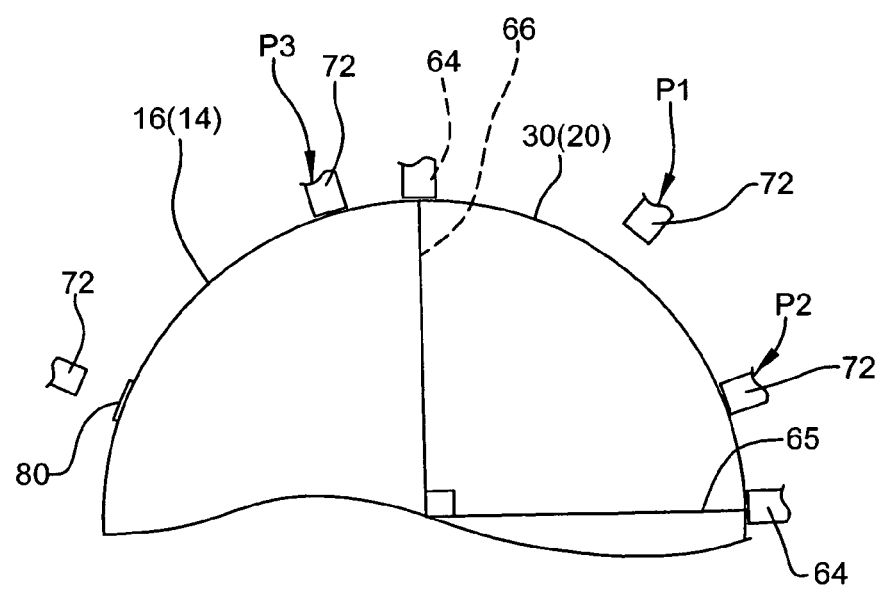
FIG. 6 is a diagrammatic end view of a machine with a vibration detector illustrated in precise horizontal and vertical orientations and a temperature detector illustrated in multiple unrestricted locations.

For each bearing location, a horizontal vibration reading 65 and a vertical vibration reading 66 are taken. Additionally, axial vibration readings 67 are taken. As seen in FIG. 6, the horizontal reading 65 is taken by the sensor 64 which is magnetically affixed to the housing 30 or 20 to avoid inadvertent sensor movement during a test. Thereafter, the vertical reading 66 is taken by the same sensor 64 wherein the phantom lines in FIG. 6 indicate a second sensor position. It is important, however, that the horizontal and vertical orientations of the sensor 64 be perpendicular to each other otherwise vibration readings would be affected. Further, solid contact of the sensor 64 with the housing 30 or 20 should be maintained to avoid movements which would introduce human error. Maintaining secure contact, however, may prove difficult for non-metallic housings.

While vibration analysis is useful in avoiding catastrophic failure of rotating equipment, such analysis also has drawbacks. In particular, each pair of bearings on a machine component requires five (5) total readings and precise positioning and orientation of the tip of the sensor 64. Further, such testing identifies problems caused by vibrations associated with rotating components although such testing does not detect problems which may cause damage but do not result in vibrations, for example, as occurs in the mechanical seal.

Still further, vibrations typically result from damage existing within the machine 12. Therefore, by the time excessive vibrations are detected, repairs may already be required for the machine 12 which will require that the machine 12 be taken out of service at least temporarily.

The temperature monitoring system of the invention, however, supplements vibration testing and improves upon the detection of problems in operating conditions before damage occurs.

More particularly as to how damage occurs, the earliest detection method is bearing oil analysis. Machine problems typically result in contaminants being found in the bearing oil. These contaminants provide the earliest warning of a problem and may be uncovered by oil analysis. However, oil analysis requires that oil samples be obtained and is a more complex testing process.

Next, heat levels begin to rise, and thereafter, vibration begins to occur once component damage occurs. Eventually, one or more machine components may fail resulting in costly repairs and downtime.

The system of the invention relates to a condition monitoring system which monitors the operating temperatures of selected components to identify abnormal operating conditions which may ultimately result in damage or failure of machine components. The monitoring system not only collects data and monitors rotating components such as bearings, but also allows for monitoring of the seal environment and fluids within the machine. This data is collected and compared to historical data from the same group of machines or to data obtained contemporaneously from different areas of the machine to provide early warning of potential problems.

The system generally involves first determining multiple temperature sensing locations on the machines, periodically collecting temperature data from such locations, and analyzing such data to identify and diagnose problems.

The temperature sensing locations are determined beforehand and physically marked on the machines. For a drive component 14 such as the motor 15, at least one and preferably two temperature sensing locations 70 are defined thereon so as to indicate the operating temperature of the motor bearings. Often, the motor near the outboard bearing has a cover which does not facilitate conduction of heat from the bearing to the cover such that a temperature measurement on the outboard motor bearing may not be feasible. As such, only one temperature reading on the drive component 14 would be taken.

As to the driven component 16 such as the pump 17, the pair of bearings 34 and 35 are typically located so as to conduct heat to the outer housing surface 39. As such, two temperature readings are usually taken from sensor locations 71 on the driven component 17.

As a result, possibly four but more likely three temperature readings associated with the bearings are taken for the motor 15 and pump 17. These readings can provide an early indication of bearing problems. Furthermore, only one temperature reading is required for each bearing thereby reducing the number of readings as compared to those required for vibration testing.

Temperature readings also are easier to obtain since the temperature reading is not dependent upon the physical orientation of a temperature sensor 72. As seen in FIG. 72, equivalent temperature readings may be taken from any of the locations identified by reference numeral 72 therein. In the first position indicated by P1, the sensor 72 is approximately one inch away from the outer housing surface, while the sensor 72 is closely adjacent to or in contact in the positions P2 and P3 respectively.

Figure 5:
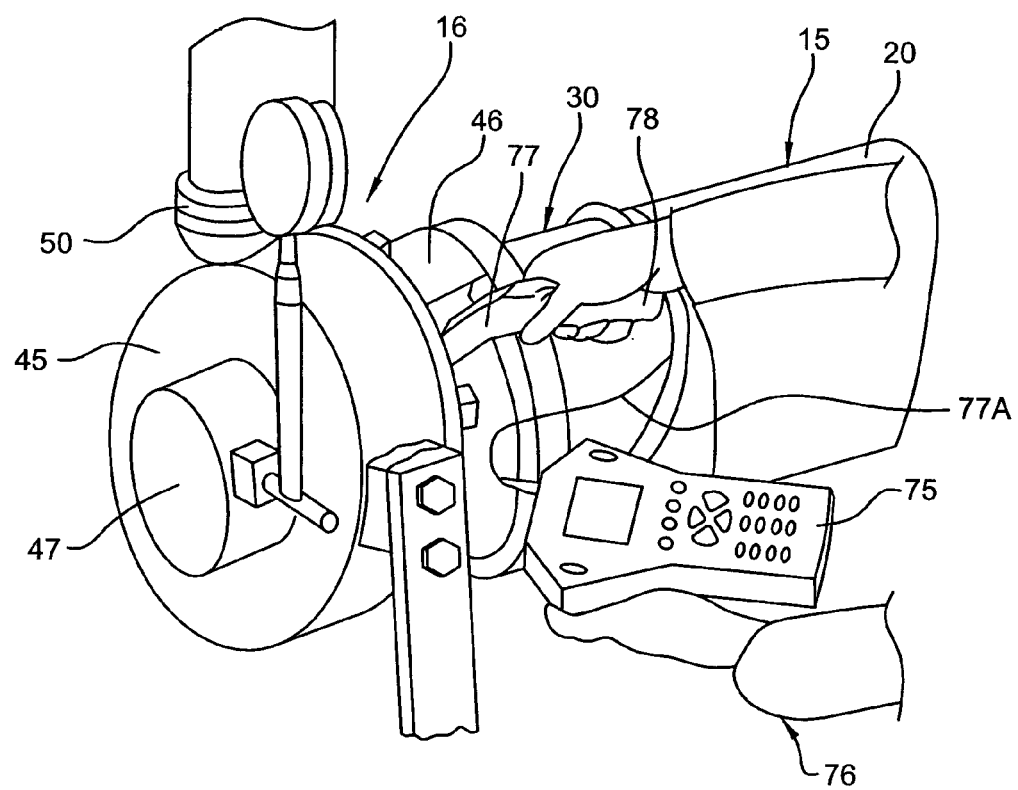
FIG. 5 is a perspective view of temperature data being collected from a machine.

The preferred data collector 75 for taking and storing temperature readings is a hand held manual data collector sold by Rockwell Automation of Milwaukee, Wis. under the model name Enpac 1200A. The Enpac 1200A is designed to download and store a predefined list of machines and to collect and store specific temperature readings for each machine 12 through a temperature sensor unit 77 attached by a cable 77A. This data collector 75 is illustrated in FIG. 5 being held by a test person or tester 76. The sensor unit 77 has a hand piece 78 that is pointed at a surface to be tested and triggered to collect a temperature reading which is stored electronically within internal storage on the data collector 75.

The primary requirement for the sensor unit 77 is that the surface being detected must be a dark surface. As seen in FIG. 6, if a dark surface is not provided, a separate plate 80 may be mounted to the housing surface being tested.

Alternatively, the plate 80 could be a bar code attached to the housing surface to provide a suitable color surface and also identify the location being tested. The sensor unit 77 of the data collector 75 reads this bar code 80 simultaneously with detection of the temperature to input both location and temperature data into the internal storage of the data collector 75.

Not only is the data collector 75 capable of detecting the operating temperatures associated with the bearings, the data collector 75 also is used to detect the operating temperature of other machine components such as the process fluid 58 and the environment of the mechanical seal. As described herein, the sensing locations associated with the process fluid 58 and mechanical seal 59 will vary depending upon the specific configuration of the machine 12 and the specific piping plan being used thereon.

When initially setting up a data collection program, a survey or audit is conducted of the machines 12 in the facility 10. The specific sensing locations are assigned for each machine 12. Further, the physical location of the machines 12 is evaluated to determine or map out the most efficient route which the human collector 76 will walk to collect the temperature data. One route 80 is diagrammatically illustrated in FIG. 1, with data collection stops 81 provided at each machine 12.

Once the sequence of machines 12 is mapped, this information is loaded into a main computer processing unit 82. In the preferred method of the invention, this processing unit 82 is located offsite and accessed through a secure internet connection 83 via an on-site computer terminal 84. The data collector 75 is plugged into a cable port on the on-site terminal 84 and the data collection route is downloaded thereto. The collector person 76 walks this route and enters temperature data at each machine 12 by aiming the sensor unit 75 at temperature sensing locations such as those associated with the bearings and mechanical seal. Each individual reading is stored in the data collector 75.

At the end of the route or data collection procedure, the collector person 76 replugs the data collector 75 into the terminal 84 and electronically uploads the data to the processing unit 82, which analyzes the data and returns a report to a facility engineer for evaluation and repair of any machines 12 having abnormal operating conditions.

It will be understood that the processing unit 82 may be eliminated and that all computer analysis may be conducted by the on-site terminal 84 through software. Furthermore, the system may be fully automated to ultimately eliminate manual collection of the temperature data.

As to the collected data, this data may be analyzed in a number of ways. Preferably such data is collected periodically, such as daily, weekly, monthly or annually. The frequency of this period will vary, for example, depending upon the critical nature of the equipment and the cost of the equipment. Upon the completion of each data collection procedure, such data is preferably compared to the historical data previously collected and stored.

Figure 7:
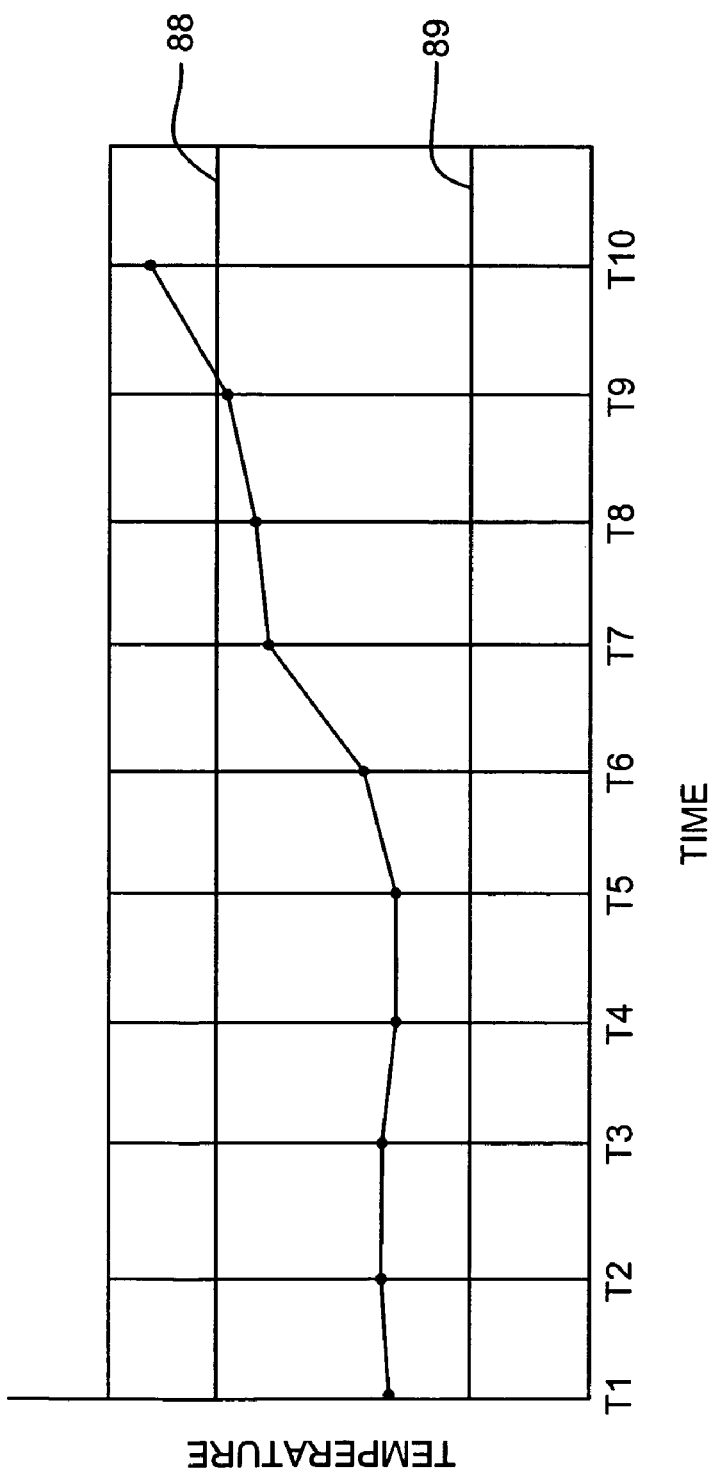
FIG. 7 is a graph of a sample temperature plot for collected temperature data.

FIG. 7 illustrates an exemplary plot of data for a single sensor location as collected over ten (10) different time periods identified T1 through T10. The temperature plot includes two parallel horizontal lines which are vertically spaced apart and generally indicate upper and lower temperature levels 88 and 89. These levels indicate basic levels which set off an alarm. However, when these levels are reached, serious component damage may already be present.

The following discusses monitoring of a temperature trend to provide an earlier indication of abnormal operating conditions. During the initial five test periods, the component temperature remained relatively steady. At the data collection period T6, an initial temperature increase was detected. At period T7, the rate of increase increased noticeably. This actual increase exceeds a predefined percentage of increase, preferably 10%, and accordingly, a warning of a 10% change is generated to prompt inspection of the component being tested. The percent change may trigger the alert either by exceeding a predefined rate or when the rate of increase is greater than the rate of increase of a previous test period which would likely indicate a worsening problem.

Therefore, at time T7, preemptive correction of a problem could be done before the temperature exceeded upper temperature limit 88. With temperature analysis, such a temperature increase, for example as in a bearing, would occur when the rotating components had suffered little if any damage. In the seal environment, the temperature increase would be detected before seal damage occurred.

If the problem is not corrected immediately, a further notice would be generated when the temperature exceeds an alarm point for the temperature. If the component temperature continues to increase, a warning level would be reached when the temperature exceeds the upper level 88 indicating the component temperature was in a danger zone where component damage or failure was emminant. This three-tiered system of monitoring temperature trends is particularly applicable for bearings. For bearings, the alert temperature would be set at 180° F. which is the temperature that the bearing oil would begin to oxidize. The final warning level would be set at 200° F.

When analyzing the temperature data, several different approaches could be taken. At a basic level, the temperature data could be used only to determine if the current temperature levels were within upper and lower limits 88 and 89. However, this might not take into account a machine that normally runs hot, unusually hot or cold environmental conditions which could elevate or decrease the component temperature, or running varying process fluids at different temperatures which also could affect the component temperature.

In view of the foregoing, it is more preferable that the last temperature data collected be compared against historical data for the same component or against contemporaneous data for different locations to diagnose a problem.

More particularly, the last temperature data can be compared against historical reference data for the same component. In one example, the reference data preferably is from the previous data collection time period as described above. In this case, T10 data would be compared against T9 data.

Alternatively, the reference data may be defined by a benchmark calculated from an average of temperature data collected over time, for example, the data collected at the beginning of the data collection program such as the data for periods T1 through T5. This benchmark would assume that the machines were in optimum operating condition wherein increases exceeding the predefined increase percentage would indicate abnormal operating conditions.

Additionally, the collected data may be analyzed for temperature trends caused by climate changes during different seasons, differences in temperatures of different process fluids, and differences in the environmental temperature of the facility 10.

In addition to this ability to compare trends in historical temperature data, the temperature data at one location may also be compared against contemporaneous temperature data and other test data at other locations.

Figure 9:
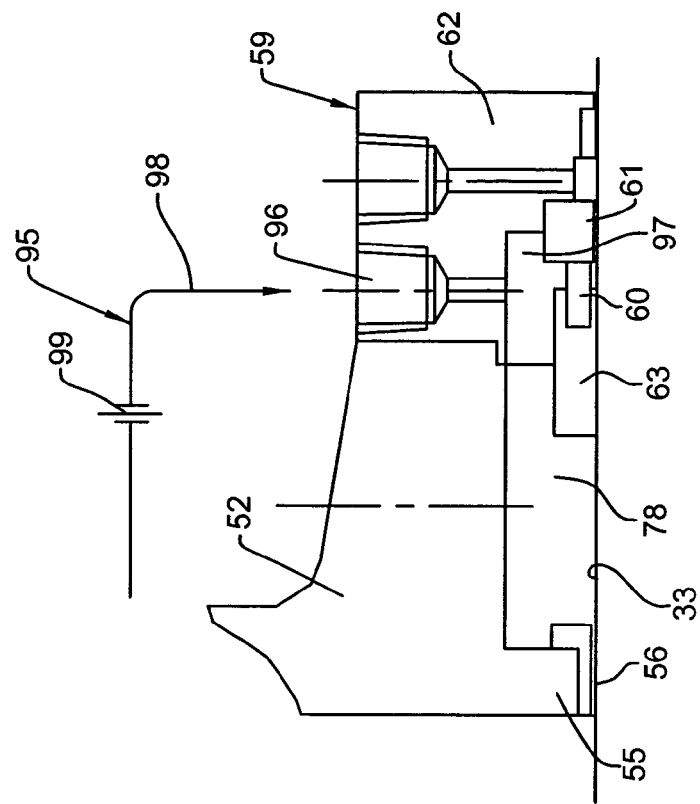
FIG. 9 is a partial cross sectional side view of the seal arrangement for the pump of FIG. 8.
Figure 8:
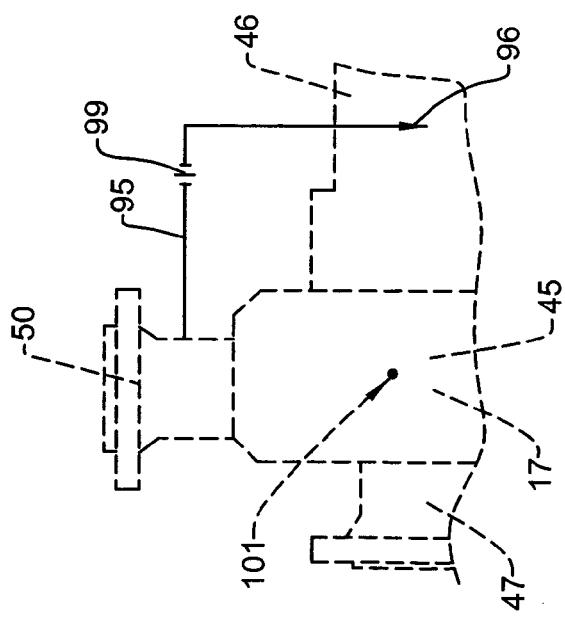
FIG. 8 is a partial side view of an API Plan 11 piping configuration for the pump.

For example, FIGS. 8–10 illustrate an API Plan 11 piping arrangement for the mechanical seal 59. This piping plan includes a bypass flush 95 which provides a flow of process fluid 58 from the pump discharge 50 to the stuffing box 52.

In particular, the seal gland 62 includes a flush inlet 96 which opens radially into a seal chamber 97 adjacent the seal rings 60 and 61. A bypass pipe 98 is connected to the discharge 50 and the inlet 96 to permit process fluid 58 to flow therethrough to flush the seal rings 60 and 61 and then flows back to the impeller chamber 49 through the throat 56. The bypass pipe 98 includes an orifice 99 to control fluid flow therethrough.

In this piping arrangement, the pump 17 and motor 15 preferably are each provided with five vibration sensing locations as described relative to FIG. 3. Further, the motor 15 has one temperature sensing location associated with the inboard bearing, while the pump 17 has two sensing locations disposed radially adjacent the bearings 34 and 35. These temperature sensing locations identify heat buildup in the bearings and preferably would be analyzed based upon a comparison of the latest temperature data with the historical temperature data for the same sensing location to identify a percentage of increase which is excessive.

Also, a sensing location 100 is defined on the bypass pipe 95 to indicate the flush temperature and a sensing location 101 is provided on the pump casing 45 to indicate the process fluid temperature in the discharge 50. Based upon contemporaneous measurements, the flush and process fluid temperatures should be proximate to each other. After a plug begins to form such as in the orifice 99, however, a drop in flush temperature relative to the process fluid temperature would occur indicating the plugged orifice 99 in the bypass pipe 95. Eventually, the temperature plot would increase due to heat generated in the seal 59 in the absence of flush caused by a plugged orifice 99. This arrangement therefore shows the method of taking a temperature reading at a single location along a flow path to identify an abnormal flow condition.

Figure 12:
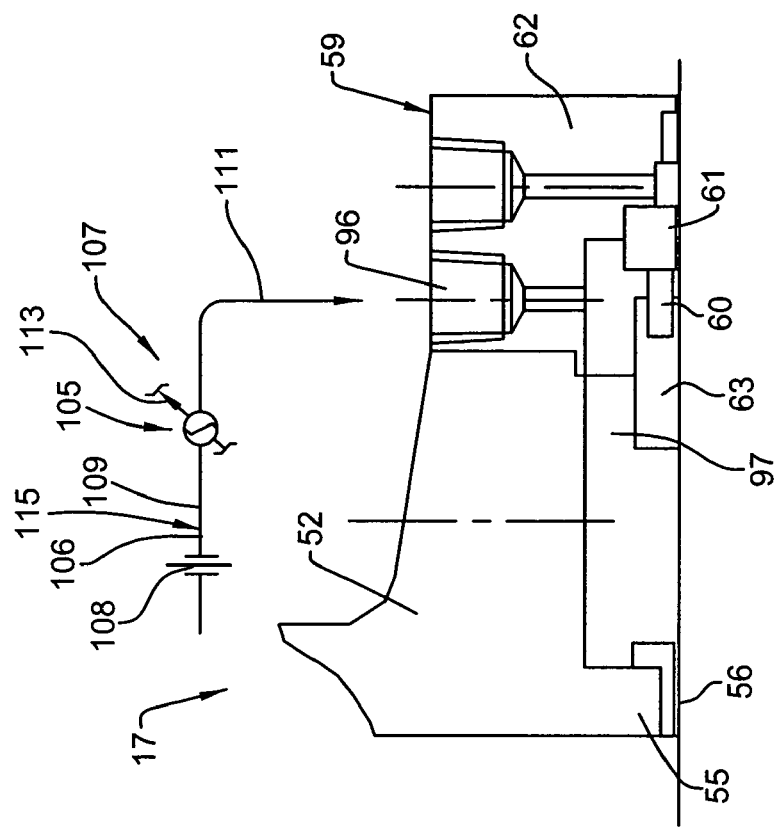
FIG. 12 is a partial cross sectional side view of the seal arrangement for the pump of FIG. 11.
Figure 11:
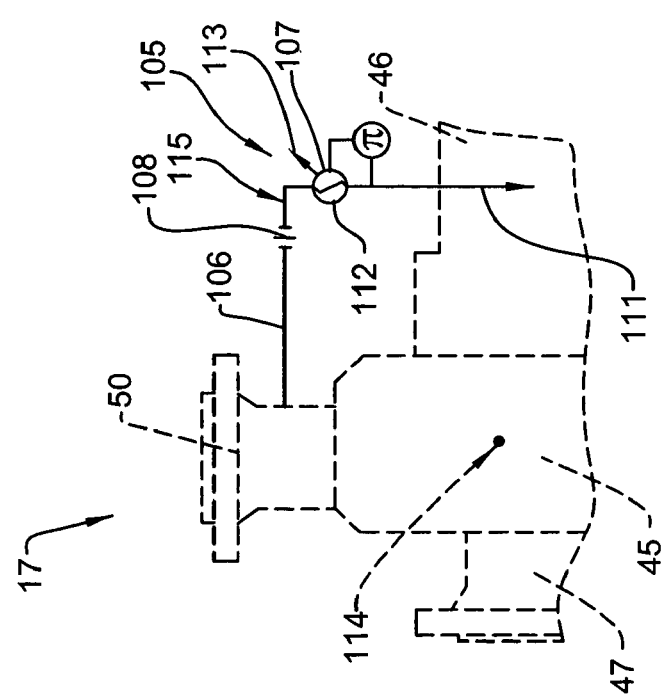
FIG. 11 is a partial side view of an API Plan 21 piping configuration for the pump.
Figure 13:
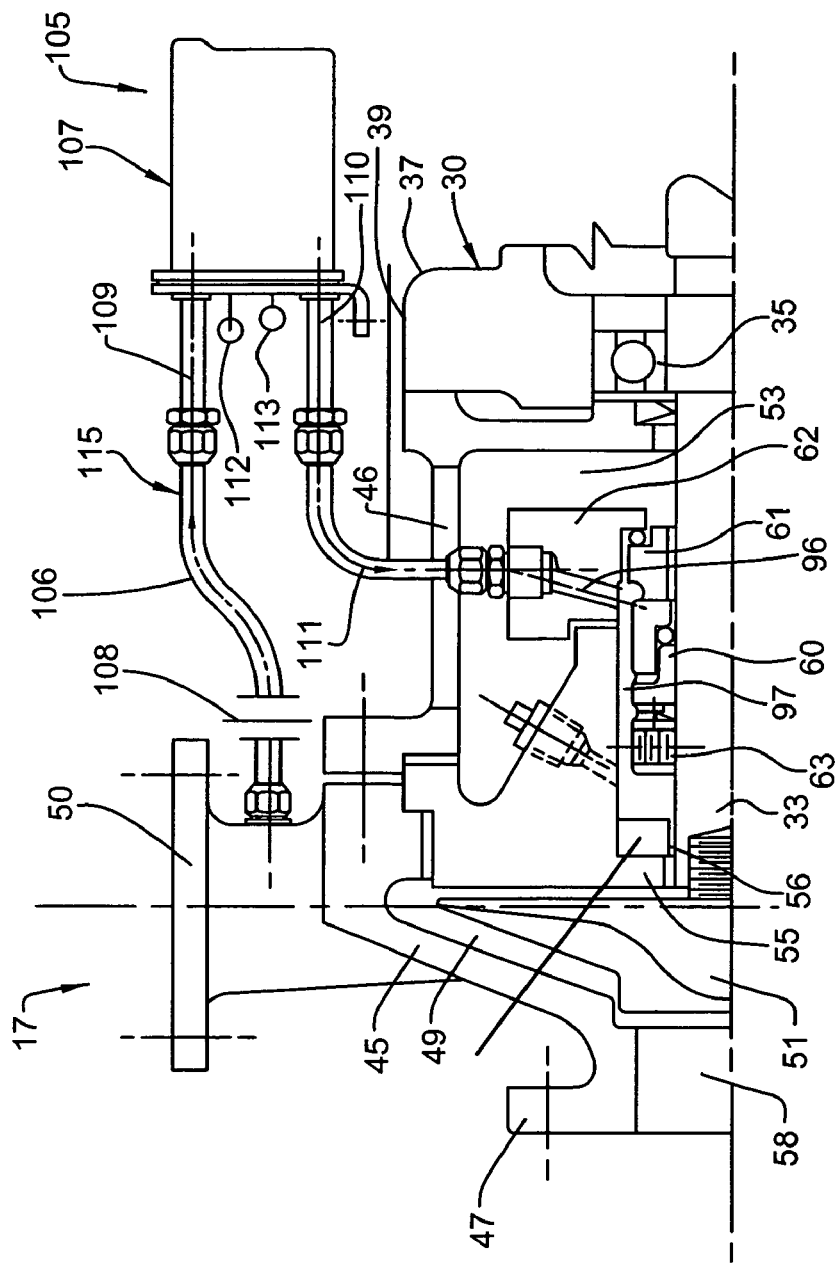
FIG. 13 is a more detailed partial cross sectional side view of the pump and seal.

FIGS. 11–13 illustrate the pump 17 with an API 21 piping plan. The pump 17 includes the seal 59 in the same arrangement as FIGS. 8–10.

In this piping plan, a seal flush arrangement 105 is provided with an upstream pipe 106 and a heat exchanger 107. The upstream pipe 106 is connected to the pump discharge 50 and includes a flow control orifice 108. Hot process fluid is supplied therethrough to the heat exchanger 107. The heat exchanger 107 includes an inlet 109 connected to the pipe 106 and an outlet pipe 110 connected to a downstream pipe 111. The downstream pipe connects to the seal inlet 96.

The heat exchanger 107 also includes a cooling water inlet 112 and a cooling water outlet 113. For temperature data collecting, the motor 15 includes one sensing location and the pump 17 includes two sensing locations for the bearings as described above. Also, a sensing location 114 is defined on the pump case 45 and another location 115 is defined on the pipe 115 to warn of plugging of the orifice 108 similar to an API Plan 11 arrangement.

Still further, sensing locations are defined on the cooling water inlet 112 and outlet 113 and the temperature readings are compared with each other based upon contemporaneous data to warn if the heat exchanger 107 is not working properly. This therefore shows an alternate data collection method of monitoring operation of a component by collecting and comparing data from upstream and downstream sensing locations.

Figure 15:
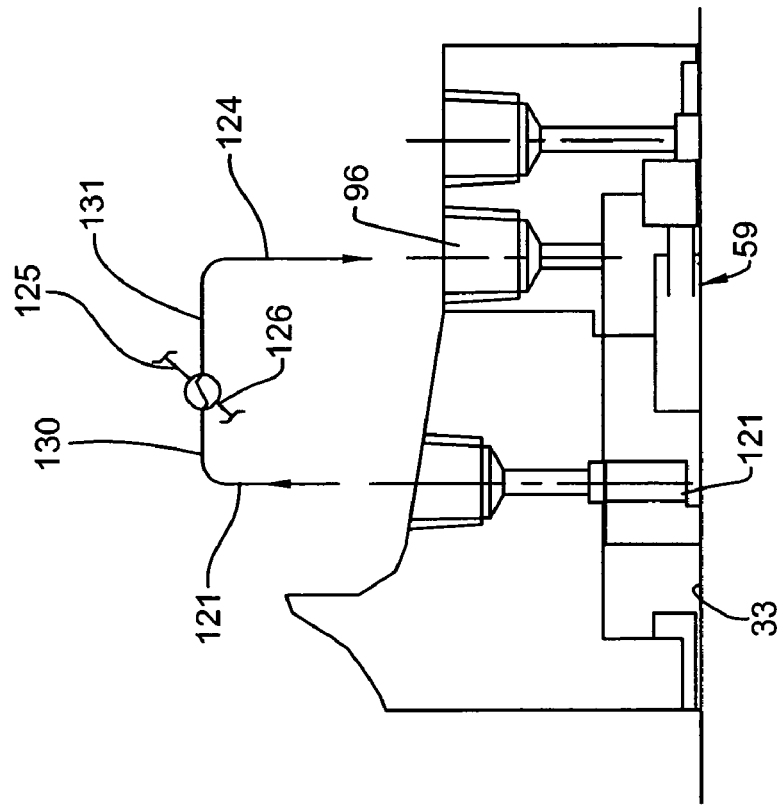
FIG. 15 is a partial cross sectional side view of the seal arrangement for the pump of FIG. 14.
Figure 14:
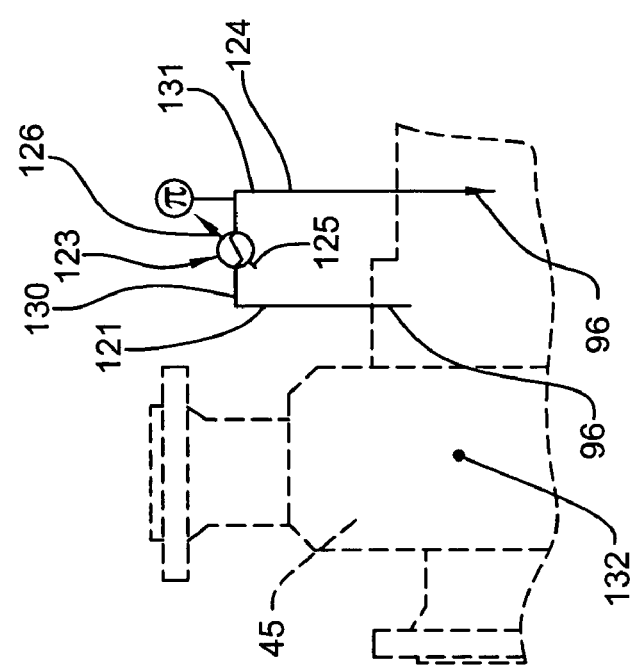
FIG. 14 is a partial side view of an API Plan 23 piping configuration for the pump.
Figure 16:
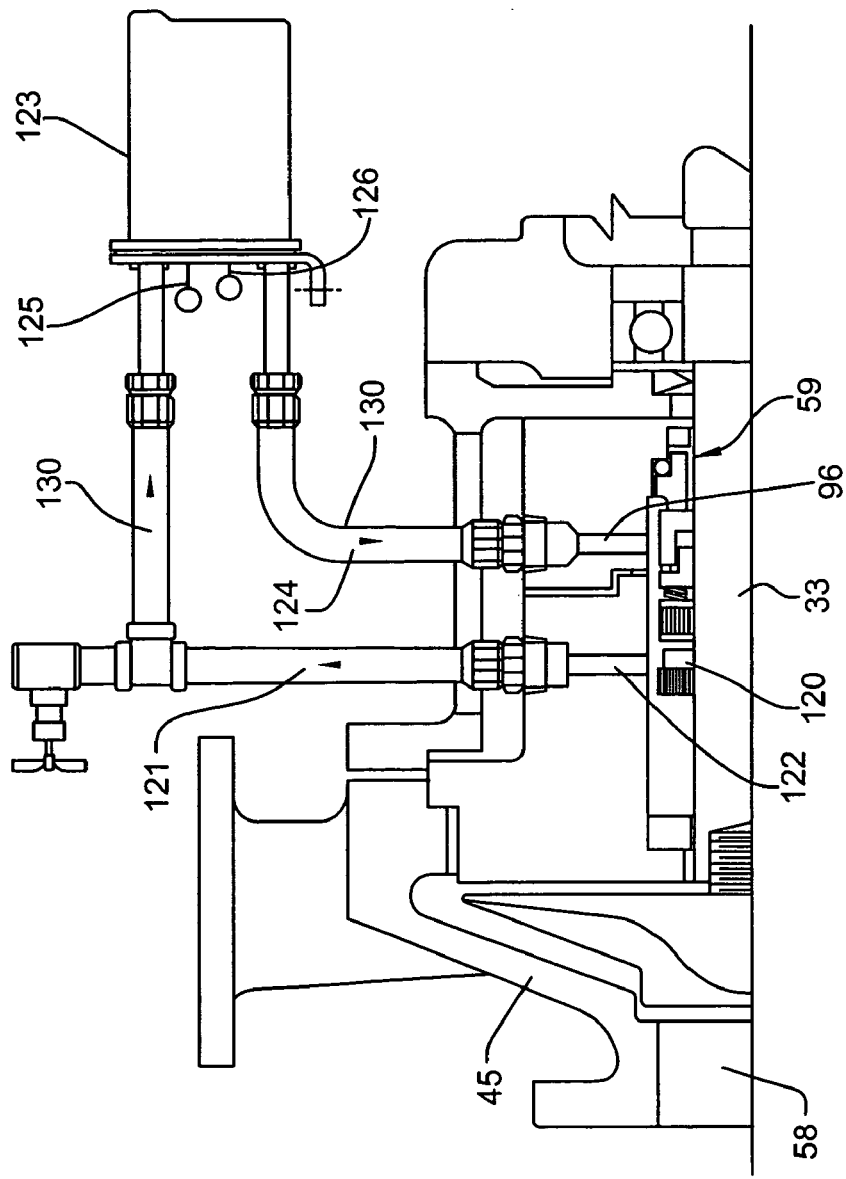
FIG. 16 is a more detailed partial cross sectional side view of the pump and seal.

Referring to FIGS. 14–16, the pump 17 has an API plan 23 piping arrangement. In this arrangement, a circulating ring 120 is provided on the shaft 33 and an outlet flush pipe 121 is connected to an outlet bore 122. Further, a heat exchanger 123 is connected to the pipe 121 as well as an inlet flush pipe 124 which pipes the flush fluid back in to the seal 59 through inlet 96. The heat exchanger 123 includes a cooling water inlet 125 and a cooling water outlet 126.

For temperature data collection, one sensing location is provided on the motor 15 and two sensing locations are provided on the pump 17 for the bearings. Further, sensing locations 130 and 131 are provided on the flush lines 121 and 124 respectively. Still further, a sensing location 132 is provided on the pump case 45 and further sensing locations are provided on the cooling water inlet 125 and outlet 125. These sensor locations indicate proper functioning of the heat exchanger 123.

Figure 18:
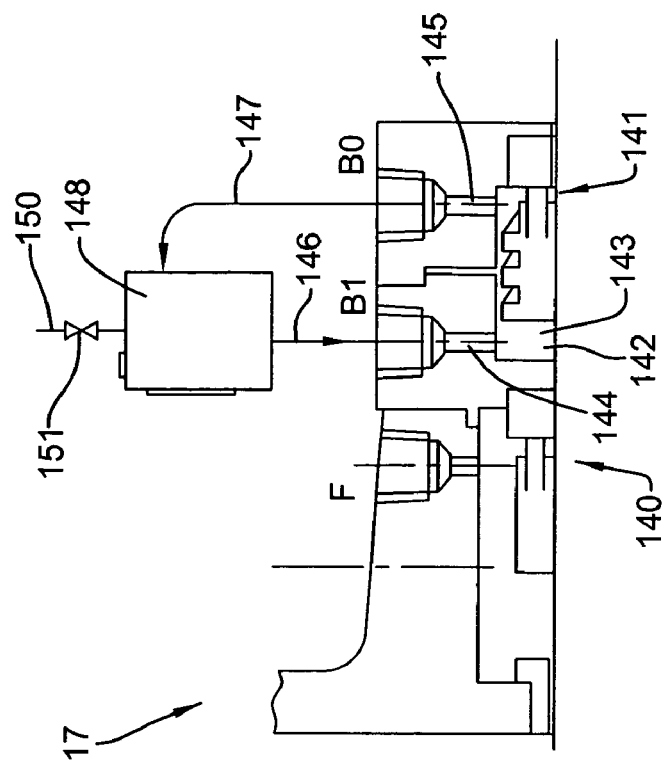
FIG. 18 is a partial cross sectional side view of the seal arrangement for the pump of FIG. 17.
Figure 17:
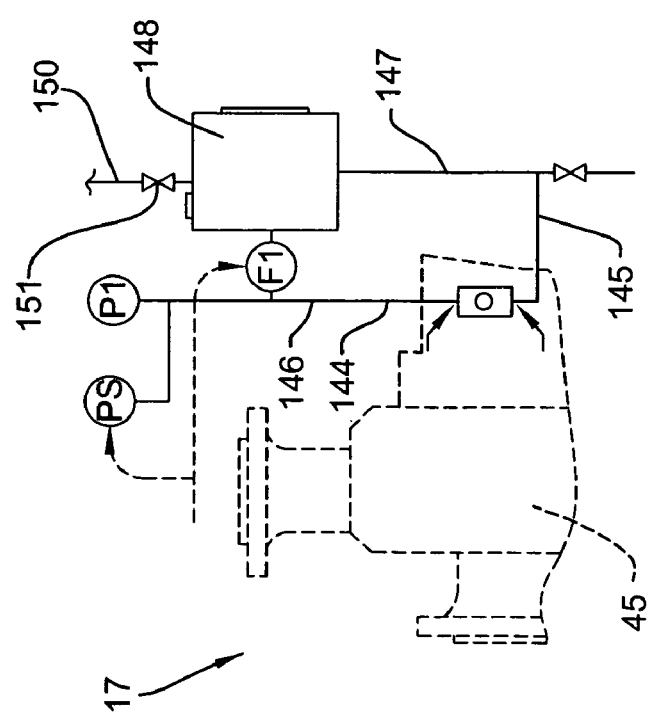
FIG. 17 is a partial side view of an API Plan 53 piping configuration for the pump.
Figure 19:
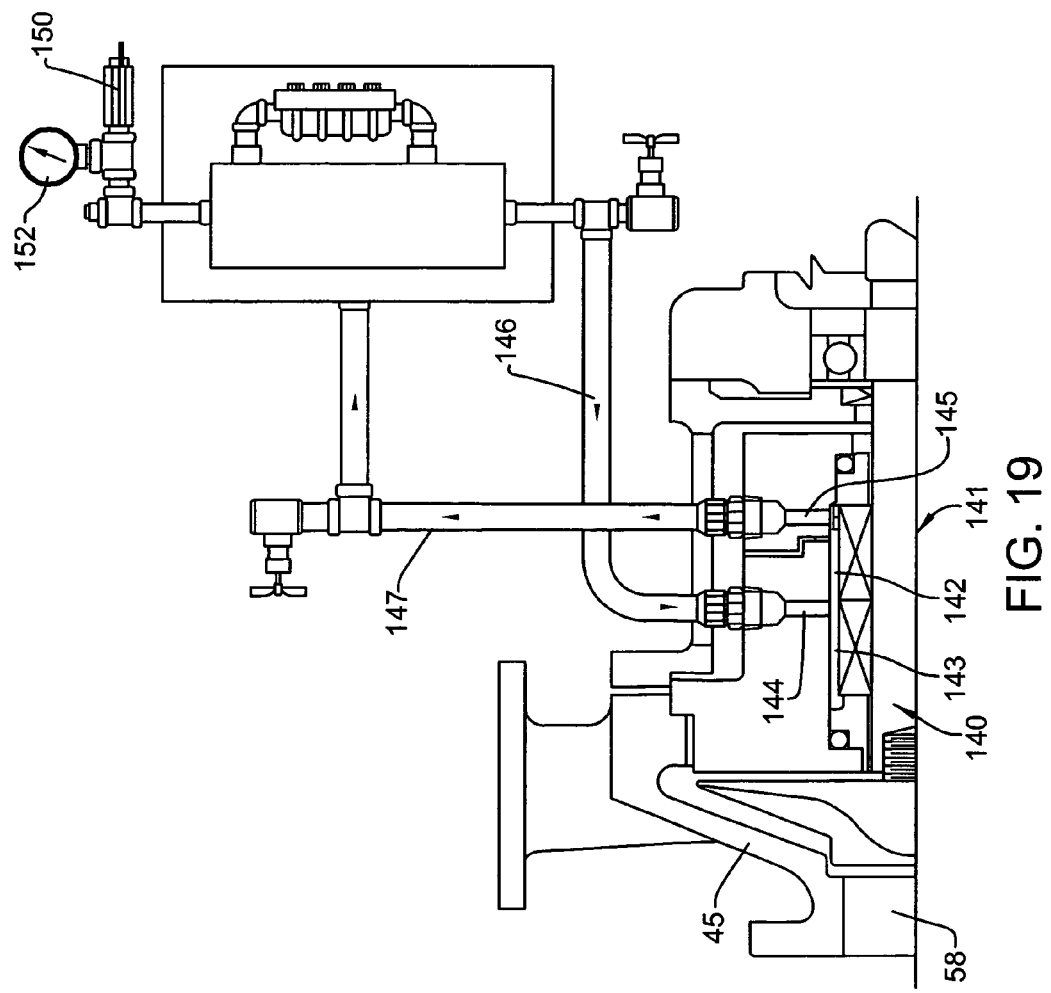
FIG. 19 is a more detailed partial cross sectional side view of the pump and seal.

Referring to FIGS. 17–19, the pump 17 has an API plan 53 piping arrangement. In this arrangement, a double seal arrangement is provide comprising an outboard seal 140 and an inboard seal 141 wherein a seal chamber 142 is defined therebetween. A pressurized barrier fluid 143 is supplied to the seal chamber 142 through a barrier fluid inlet 144 and a barrier fluid outlet 145. The inlet 144 and outlet 145 are connected respectively to inlet and outlet pipes 146 and 147 which are further connected to a barrier fluid supply tank 148 to define a closed loop fluid supply system.

Further, a pressure source 150 is connected to the supply tank 148 and a block valve 151 may be provided thereon as seen in FIGS. 17 and 18 and a pressure gauge 152 provided as seen in FIG. 19. A pressure switch, pressure gauge and flow indicator also may be installed on the inlet pipe 146.

For temperature data collection, one sensing location is provided on the motor 15 and two sensing locations are provided on the pump 17 as described above. Further, temperature sensing locations may be defined on the barrier fluid in and barrier fluid out lines 146 and 147 to confirm proper flow of barrier fluid based upon a comparison of contemporaneous data from the different sensing locations. Further, data collection also includes the barrier fluid level and barrier fluid pressure to confirm proper operation thereof since low fluid levels and low pressure levels may be the cause of high temperature readings elsewhere in the seal system.

These plans are examples of data collection methods for the seal environment. These piping plans also may be combined. For example, a bypass flush of API Plan 11 could be added to the Plan 53 seal of FIGS. 17–19 at which time temperature data would be taken for the pump case 45 and a bypass flush line as in FIG. 8.

In operation, the method for monitoring operating conditions is performed on rotating equipment which rotating equipment comprises the drive component 14 having the rotating drive shaft 24 in the driven component 16 having the shaft 33 and a rotating part connected to the shaft 33. The rotating part may be a pump impeller 51 or the like. The rotating equipment further includes bearings therein which rotatably support the shafts 24 and 33 and the rotating part thereon. The rotating equipment also includes a process fluid and a primary mechanical seal preventing leakage of the process fluid along the shaft 33. The mechanical seal includes passages therein containing a seal fluid such as a gland flush, barrier fluid or cooling water.

The method comprises the steps of providing the temperature data collector 75 having the temperature source 77, and defining temperature sensing locations on the rotating equipment. The sensing locations are defined on the bearings and/or on the seal passages. Each temperature sensing location 70 or 71 associated with a bearing indicates an operating temperature of the associated bearing, and each sensing location associated with a seal passage indicates a temperature of a seal fluid such as the flush, barrier fluid or cooling water.

The method further includes the steps of performing a temperature data collection procedure on the rotating equipment which comprises the steps of manually positioning the temperature sensor 77 adjacent the rotating equipment, detecting surface temperatures on the rotating equipment by temperature readings of the sensing locations through the temperature sensor 77, and storing temperature data from each said temperature reading in the data collector 75. This data collection procedure is repeated periodically over time to develop historical data for each sensing location. Thereafter, the temperature data is analyzed by comparing each temperature data from a last data collection procedure with reference temperature data to identify temperature increases in the rotating equipment that indicate abnormal operating conditions of the bearings and/or the seal arrangement.

The reference temperature data may be defined by the temperature data of at least one prior data collection procedure wherein a plurality of prior data collection procedures may be performed and the results averaged to generate the reference temperature data. Alternatively, the prior data collection procedure may be defined by one data collection procedure performed immediately prior to the last collection procedure.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method for monitoring operating conditions on one or more units of rotating equipment disposed within a facility which rotating equipment comprises a drive component having a rotating shaft and a driven component having a rotating part connected to said shaft, said rotating equipment including bearings therein which rotatably support said shaft and said rotating part thereon, and said rotating equipment including a process fluid and a shaft seal arrangement having a mechanical seal that comprises seal rings cooperating with said shaft which are relatively rotatable and prevent leakage of said process fluid along said shaft, said seal arrangement including a fluid chamber adjacent said seal rings and passages containing a passage fluid supplied to said that fluid chamber of said mechanical seal such that said passage fluid circulates through said fluid passage to maintain an operating temperature of said seal rings, said rotating equipment further including external exposed surfaces respectively adjacent said bearings and said passages wherein each of said exposed surfaces has a surface temperature defined by the operating conditions of said respective bearing or passage fluid which said surface temperatures vary in response to the operating conditions of said bearings and said shaft seal arrangement, the method comprising the steps of:

providing a temperature data collector which is manually movable within said facility by an operator, said temperature data collector having a temperature sensor which is manually positionable within said facility by said operator to detect said surface temperatures of said rotating equipment, said temperature data collector further including a data storage unit which receives and stores temperature data from said sensor;

defining temperature sensing locations on said rotating equipment, said sensing locations being defined on said exposed surfaces adjacent said bearings and said passages, each said temperature sensing location associated with a said bearing indicating an operating temperature of said associated bearing, and each said sensing location associated with a said passage indicating a temperature of said passage fluid therein;

preforming a temperature data collection procedure on said rotating equipment, said temperature data collection procedure comprising the steps of manually transporting said temperature data collector within said facility to an equipment location proximate each said unit of said rotating equipment and manually positioning said temperature sensor adjacent to said sensing locations on said rotating equipment, detecting surface temperatures on said rotating equipment for said bearings and said passage fluid by temperature readings of said sensing locations through said temperature sensor, and storing temperature data from each said temperature reading in said data storage unit of said data collector;

repeating said data collection procedure periodically over time to detect and store said temperature data at periodic time intervals by manually transporting and returning said temperature data collector to said equipment location and repositioning said temperature sensor adjacent to said sensing locations;

said data collection procedure further including the step of removing said temperature sensor from said equipment location by manually moving said temperature data collector to another location in said facility; and analyzing said temperature data by comparing each said temperature data from a last said temperature data collection procedure performed with reference temperature data to identify temperature increases in said rotating equipment indicating abnormal operating conditions of said bearings and said shaft seal arrangement when said increases exceed an acceptable amount as compared to said last temperature data collection period and then performing preemptive repair based on said abnormal operating conditions indicated by said temperature increases.

2. The method according to claim 1, wherein said method further comprises the steps of providing a remote processing station separate from said rotating equipment, and transferring said temperature data from said data storage unit of said temperature data collector where said processing station performs said analyzing step.

3. The method according to claim 2, wherein said data collection procedure includes the step of manually relocating said temperature data collector to said processing station for said transferring of said temperature data thereto, said transferring of said temperature data being performed prior to performance of the next said data collection procedure.

4. The method according to claim 2, wherein said processing station is a computer disposed within said facility.

5. The method according to claim 1, wherein a plurality of said units of said rotating equipment are provided which define a plurality of said equipment locations, said temperature data collector being moved from one said equipment location to a next said equipment location during said temperature data collection procedure to detect said surface temperatures of said bearings and said passage fluid for each of said units.

6. The method according to claim 1, wherein said temperature data collector is a handheld unit comprising said temperature sensor and said data storage unit which are disposed within said handheld unit so as to be moved together by the operator.

7. The method according to claim 1, wherein said passage fluid is supplied from said process fluid and an increase in said temperature of said passage fluid is caused by heat generation from said seal rings.

8. A method for monitoring the operating conditions of a plurality of units of rotating equipment within a facility, said rotating equipment including relatively rotatable parts which comprise a rotating shaft, bearings which support the shaft, and a shaft seal assembly comprising a mechanical seal which includes relatively rotatable seal rings, said seal rings sealing a sealed fluid within said rotating equipment during shaft rotation to prevent said sealed fluid from leaking along said shaft, said rotating equipment including a fluid chamber adjacent said seal rings and a fluid passage in open communication with said fluid chamber wherein a passage fluid flows between said fluid chamber and said fluid passage and along said seal rings to maintain an operating temperature of said seal rings, said rotating equipment having exterior surfaces which have surface temperatures which indicate the respective operating temperatures of the bearings and the shaft seal assembly, the method comprising the steps of:

providing a portable temperature data collector which is manually movable within said facility by an operator, said temperature data collector including a temperature sensor which is manually positionable adjacent to said exterior surfaces to detect said surface temperatures of said exterior surfaces associated with said bearings and with said passage fluid of said shaft seal assembly and which generates temperature data indicating said surface temperatures detected thereby, said sensor communicating with a data storage unit which receives and stores said temperature data for subsequent analysis;

defining temperature sensing locations on said rotating equipment respectively corresponding with each of said rotatable parts wherein said surface temperature on said rotating equipment at each said sensing location indicates the operating temperature of said respective rotating part corresponding thereto, at least one of said temperature sensing locations being adjacent said passage spaced from said seal rings;

preforming a temperature data collection procedure on said rotating equipment at a collection time to determine the operating temperatures of said respective rotatable parts at said collection time, said temperature data collection procedure comprising the steps of manually transporting said temperature data collector within said facility to an equipment location proximate each said unit of said rotating equipment being monitored, manually positioning said temperature sensor adjacent to a plurality of said sensing locations, detecting said surface temperatures of said exposed surfaces at said plurality of said sensing locations with said temperature sensor and generating said temperature data corresponding to each of said sensing locations corresponding to said bearings and said passage fluid of said mechanical seal, storing said temperature data for said bearings and said mechanical seal in said data storage unit, and manually removing said temperature data collector from each said equipment location after obtaining said temperature data for said sensing locations within said equipment location;

repeating said data collection procedure at subsequent collection times to detect and store said temperature data for each said collection time wherein said collection times are spaced from each other by selected time intervals and said temperature data collector is transported to each said equipment location and then removed therefrom at the end of each said data collection procedure;

storing said temperature data associated with each of a plurality of collection times to develop historical data for each said sensing location; and analyzing said historical data by comparing the temperature data from a last said temperature data collection procedure with the temperature data from a prior said data collection procedure to identify abnormal increases in said operating temperatures of said rotatable parts wherein said abnormal temperature increases exceed a defined amount when compared to said prior data collection procedure, and wherein said increase in said temperature of said passage fluid is caused by heat generation from said seal rings; and operating said rotating equipment in response to any said abnormal increases identified by said abnormal temperature increases identified by said analysis in said bearings and said shaft seal assembly.

9. The method according to claim 8, which includes the step of providing a processing unit which receives said temperature data and analyzes said historical data.

10. The method according to claim 9, which includes the step of transferring said temperature data to said processing unit after each said temperature data collection procedure.

11. The method according to claim 10, which includes the step of connecting said temperature data collector to said processing unit for said transferring of said temperature data.

12. The method according to claim 8, wherein one said sensor is used for detecting temperature at a plurality of said sensing locations.

13. The method according to claim 8, wherein said sensor is a portable sensor which is manually directed toward each said sensing location to detect said surface temperatures.

14. The method according to claim 8, wherein each temperature data collection procedure at each said collection time includes positioning said temperature sensor at a plurality of said equipment locations corresponding to a plurality of units of said rotating equipment such that said temperature data for each said collection time relates to said plurality of said units of said rotating equipment.

15. The method according to claim 14, wherein said temperature data for said plurality of said units of said rotating equipment is stored in said data storage unit until the end of said temperature data collection procedure.

* * * * *